United States Patent [19]
Schmedemann

[11] Patent Number: 4,603,845
[45] Date of Patent: Aug. 5, 1986

[54] X-RAY UNIT WHICH CAN BE SWIVELLED ABOUT A HORIZONTAL AXIS

[75] Inventor: Walter Schmedemann, Tangstedt, Fed. Rep. of Germany

[73] Assignee: U.S. Philips Corporation, New York, N.Y.

[21] Appl. No.: 596,783

[22] Filed: Apr. 4, 1984

[30] Foreign Application Priority Data

Apr. 18, 1983 [DE] Fed. Rep. of Germany ....... 3313994

[51] Int. Cl.⁴ .............................................. H01J 37/20
[52] U.S. Cl. ..................................... 269/323; 378/209
[58] Field of Search .................... 269/322, 323; 108/4, 108/5, 6, 7, 8; 378/209

[56] References Cited

U.S. PATENT DOCUMENTS

| 3,240,935 | 3/1966 | Dougall | 378/209 |
| 3,525,308 | 8/1970 | Koopmans | 269/323 |
| 3,805,080 | 4/1974 | Yager et al. | 269/323 |

FOREIGN PATENT DOCUMENTS 464958  3/1952  Italy .................................... 378/209

Primary Examiner—Robert C. Watson
Attorney, Agent, or Firm—Marc D. Schechter

[57] ABSTRACT

The invention relates to an X-ray unit which can be swivelled about a horizontal axis. The table is moved by a lever arrangement in which the longitudinal position of the table is a function of the swivel angle so that a greater low head position can be achieved.

4 Claims, 4 Drawing Figures

X-RAY UNIT WHICH CAN BE SWIVELLED ABOUT A HORIZONTAL AXIS

BACKGROUND OF THE INVENTION

The invention relates to an X-ray unit with a table top and a supporting frame. The frame is supported so as to move in the longitudinal direction by a guide which is mounted on a pedestal. The guide is mounted on the pedestal so as to swivel about a horizontal swivel axis. A swivel motion of the guide can be converted by a lever arrangement and a connecting rod into a longitudinal movement of the table top.

Such a unit can be swivelled into a position in which the table top is vertical (a low foot position), and can be swivelled out of this position through the horizontal position into a so-called low head position. Because the swivel axis must be relatively low, it is necessary, when swivelling the table top, to move the frame within the guide in the longitudinal direction of the table in such a way that the table does not collide with the floor in the two extreme swivel positions.

An X-ray unit of the type described above is described in DE-PS No. 970 321. The frame is moved in this unit by a connecting rod coupled to a lever arrangement. As a result, the swivel motion of the guide produces a longitudinal movement of the table supporting frame. The lever arrangement in the known unit is, of course, only effective when the frame is swivelled through the horizontal position into the low head position. In this case, a cam mounted on the guide acts on the lever arrangement. The activation of the lever arrangement by the cam is sudden, resulting in shaking of the unit. If the unit is swivelled through the horizontal position in the direction of the foot end, the cam no longer acts on the lever arrangment, and the frame can be moved freely in the direction of the head end (i.e. its position is then independent of the swivel position of the unit).

SUMMARY OF THE INVENTION

It is an object of the present invention to design an X-ray unit (examination table) in such a way that there is no longer a jolting transfer when the table top is tilted toward the low head position, and in which the position of the frame is uniquely defined by the swivel position of the guide.

The invention achieves this object by providing the lever arrangement with a two-arm lever. The two-arm lever is mounted on the guide at a distance from the switch axis. A rod-like element is arranged on the pedestal so as to swivel about an axis parallel to the swivel axis. The free ends of the rod-like element and the connecting rod are articulated with the two lever arms.

The rod-like element, the lever arm connected to it and the rigid connections (formed the guide) between the points of support of the rod-like element and the lever arm and the swivel axis form a four bar linkage. The four bar linkage is driven by the swivel of the guide. The lever arm rotates about its support point. This rotary movement is transmitted to the other lever arm and to the connecting rod. The other lever arm and the connecting rod together form a so-called thrust crank, by means of which the frame is moved within the guide.

Because all the parts here (the frame, the guide, and the pedestal) are coupled to one another via rigid power transmission elements, the frame assumes a single definite position relative to the guide for each swivel angle. Because all the power transmission elements are active all the time, the jolting changeover which occurs in the known unit when the cam engages with the lever arrangement is avoided.

DESCRIPTION OF THE PREFERRED EMBODIMENTS

Figure 1:
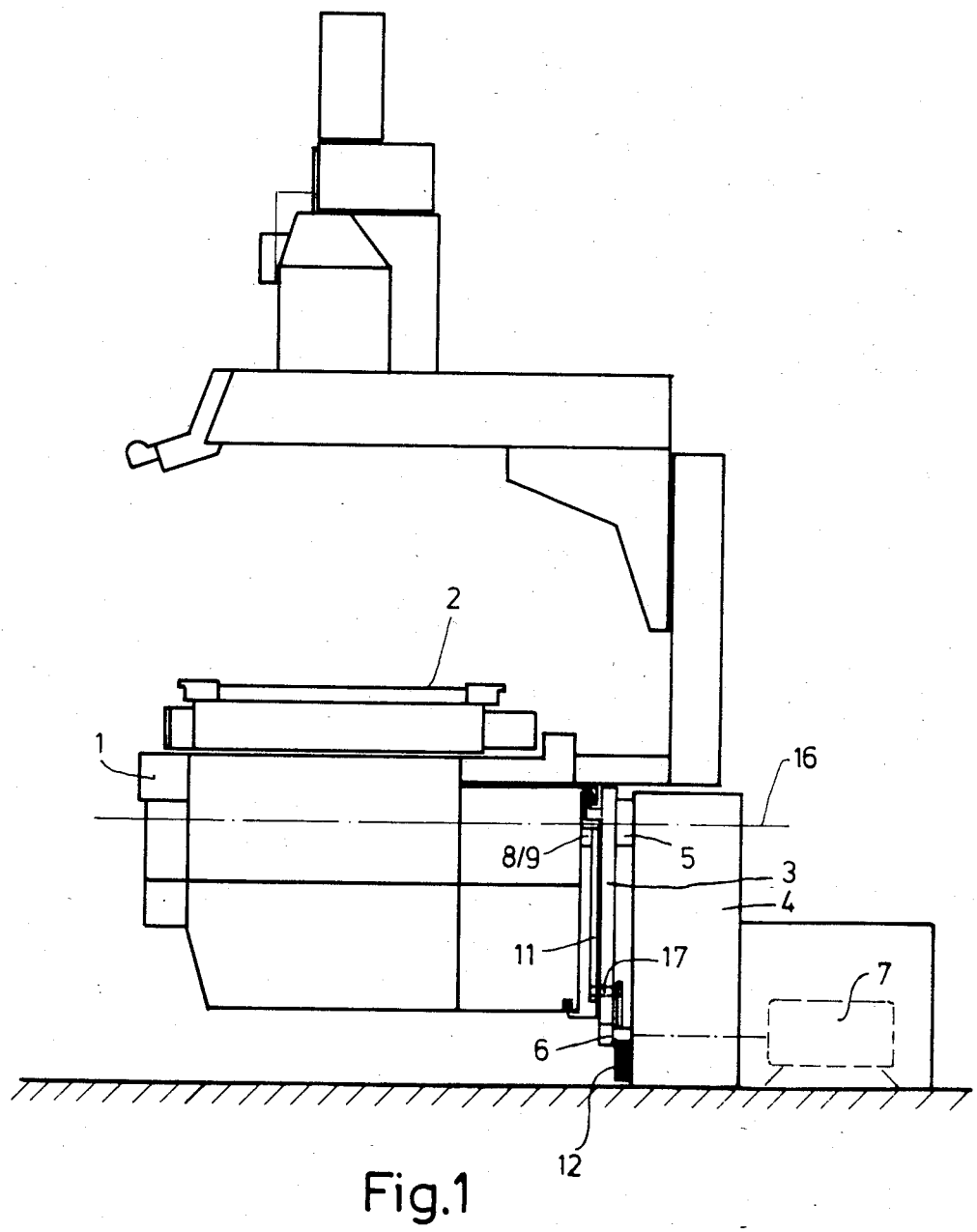
FIG. 1 is a front elevational view of the X-ray unit (from the foot end) with the frame in the horizontal position.

The X-ray unit (examination table) shown in FIG. 1 comprises a frame 1 which supports a table top 2. Frame 1 can be moved in a guide 3 in the longitudinal direction of the table top (i.e. at right angles to the plane of FIG. 1) and is supported by guide 3.

The guide 3 is connected to a pedestal 4 on which the entire weight of the unit rests. The guide 3 is mounted on a bearing 5 so that the guide can be swivelled about the horizontal axis 16. Axis 16 extends perpendicular to the longitudinal direction of the table and passes through the center of bearing 5.

The guide 3 is a solid semicircular segment. The center of curvature of the guide 3 coincides with the swivel axis 16. Guide 3 is provided on its external periphery with teeth which are engaged by a drive pinion 6. Drive pinion 6 is driven by a drive motor 7.

Figure 2A:
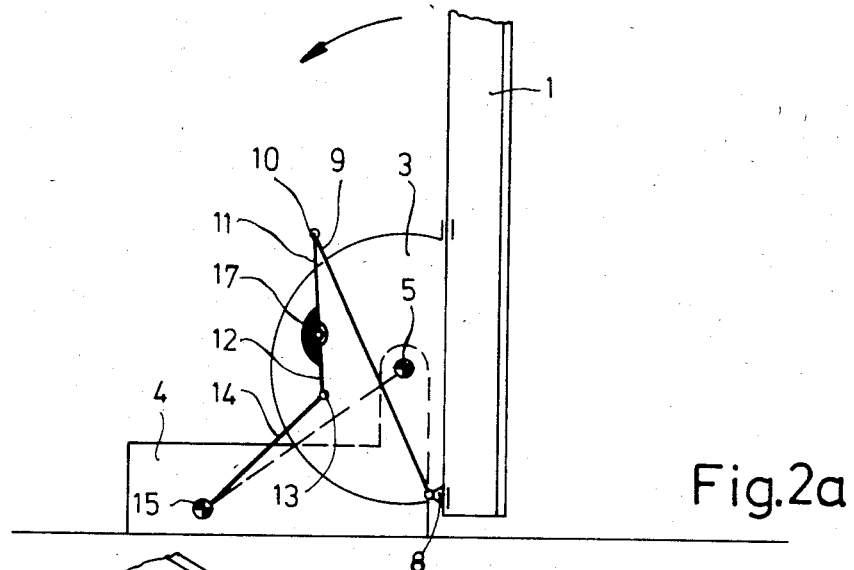
FIGS. 2a to 2c are schematic side views, at different swivel angles, of the X-ray unit. The parts which are not essential for understanding the invention have been omitted.
Figure 2B:
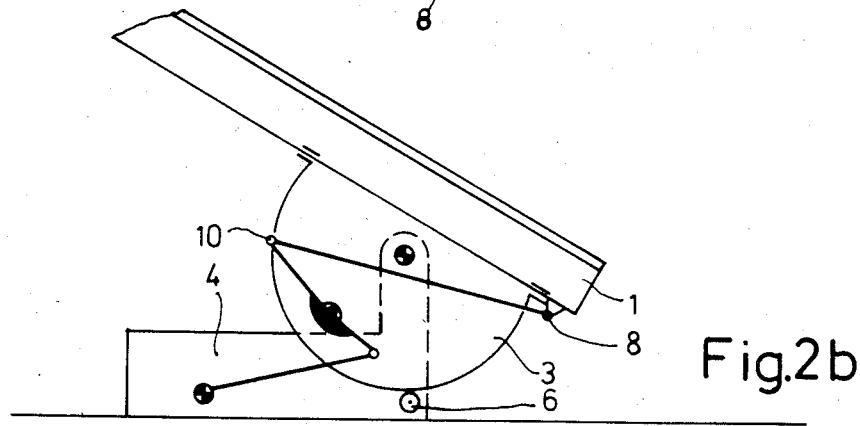
Figure 2C:
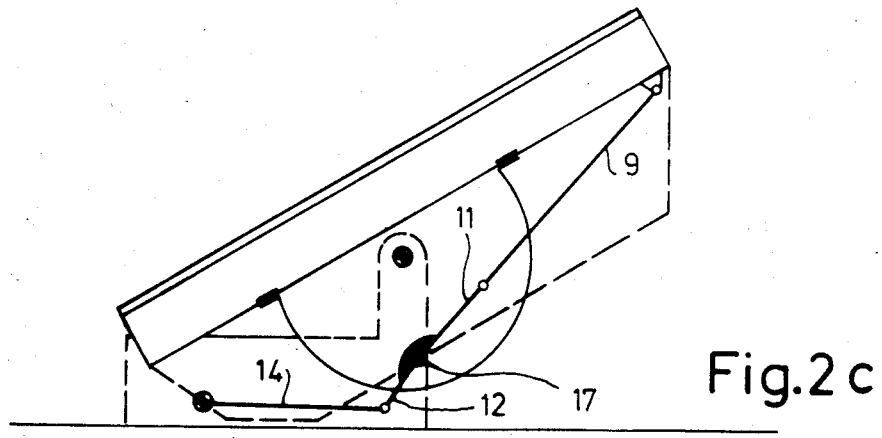

FIGS. 2a to 2c show the X-ray unit of the invention in a vertical tabletop position (FIG. 2a), in a position slightly inclined toward the foot end (FIG. 2b), and in the maximum achievable low head position (FIG. 2c). At the foot end of the frame 1 there is articulated at 8 a connecting rod 9. Connecting rod 9 is connected at its other end 10 to one arm 11 of a two-arm lever. The other arm 12 of the two-arm lever is articulated at 13 with a rod 14. Rod 14, in turn, can be pivoted about a swivel joint 15 on the pedestal 4.

The two-arm lever (i.e. of the two lever arms 11 and 12) is supported at 17 in the guide 3 at a distance from the bearing 5. When the unit is swivelled, the bearing 17 moves on an arc around the bearing 5 or the horizontal swivel axis 16.

The rod 14, the lever arm 12, the rigid connection formed by the guide 3 between the bearings 5 and 17, and the rigid connection formed by the guide 3 between the bearings 5 and 15 form a four-bar linkage. The linkage 5–17 forms the driven element (the so-called crank) the lever arm 12—forms the "coupler", and the rod 14 forms the so-called "rocker".

The swivelling of the lever arm 12 about the bearing 17 is transmitted to a so-called thrust crank. The thrust crank is formed by the lever arm 11 and the connecting rod 9. The lever arm 11 represents the drive element (which itself is driven by the lever arm 12), and the connecting rod 9 forms the driven element. Rod 9, in turn, moves the frame 1 in a straight line relative to the guide 3.

As follows from the above, the frame 1 is moved only when the two-arm lever is rotated about its bearing 17. Such a rotation would not occur, if during a swivel motion of the X-ray unit the articulation 13 (between the rod 14 and the lever arm 12) rotated on a circle about the bearing 5 or the swivel axis 16 (FIG. 1). If the path of the articulation deviates only slightly from such a circular path, the rotation of the levers 11 and 12 about bearing 17 is slight, and therefore the movement of the frame 1 within the guide 3 is also slight.

As FIG. 2a shows, in the vertical position of the unit the angle between the rod 14 and the straight line connecting the points 5 and 15 is relatively small. Consequently, when the guide 3 is swivelled out from this position toward the horizontal position, the articulation 13 moves on a circle around the bearing 15. This circle is approximately coincident with a circle about the bearing 5, so that when the guide 3 is swivelled from the low foot position illustrated in FIG. 2a, the lever 12 is scarcely rotated and the frame 1 is scarcely moved on guide 3 in the longitudinal direction. Furthermore, in this position the angle between the level arm 11 and the connecting rod 9 joined is relatively acute so that rotation of the lever 11 and 12 about the bearing 17 has only a slight effect on the movement of the frame 1 along guide 3 in the longitudinal direction.

The result of all this is that when the unit is swivelled out of the position illustrated in FIG. 2a into the position illustrated in FIG. 2b the frame 1 is scarcely moved in the longitudinal direction, so that as a result of the movement it also cannot collide with the floor.

If the table is further swivelled (from the position in FIG. 2b) in a counterclockwise direction, however, the conditions change substantially. When the table is nearly horizontal, the articulation 13 moves on an arc which is almost perpendicular to a circle about the bearing 5. As a result, the lever 11 and 12 is rotated relatively strongly about the bearing 17. At the same time, the angle between the lever arm 11 and the connecting rod 9 is approximately 90°.

As a result of these conditions, when the table is nearly horizontal there is a relatively large movement of the frame with respect to the swivel of the unit. This means that the predominant part of the longitudinal movement occurs when the table is nearly horizontal. This is advantageous because in this position the weight of the table frame only slight affects the forces required for moving the table.

FIG. 2c shows the unit in its extreme low head position. For clarification, the contours of the panelling of the table frame are indicated by a dashed line. The thrust crank formed by the lever 11 and the connecting rod 9 is fully stretched.

As FIGS. 2a to 2c show, the lever 11 and 12 is slightly angled (i.e. the lever 11 forms an angle of less than 180° with the lever 12, measured in the clockwise direction). This slight angling prevents the arm 11 from projecting beyond the outline of the unit when the unit is in the erect position.

As FIG. 1 shows, the frame 1 and the pedestal 4 are arranged on different sides of the segmentshaped guide 3. Because the connecting rod 9 must engage the frame 1, but the rod 14 has to engage the pedestal 4, the connecting rod 9, the lever arms 11 and 12, and the rod 14 cannot all be in the same plane. For this reason, the lever arm 11 and the connecting rod 9 are arranged between the guide 3 and the frame 1. The lever arm 12 and the rod 14 are arranged between the guide 3 and the pedestal 4.

The lever arms 11 and 12 are rigidly connected to one another via the bearing 17 through the guide 3. This arrangement has the advantage that the lever arm 11 can be longer than—if it were on the other side of the guide 3 (where it would collide with the bearing 5). This assumes, of course, that in the vertical position of the lever arm 11 the frame 1 is guided in the guide above the articulation 10.

A unit which has been practically tested had the following dimensions:

| | |
|---|---|
| Connecting rod 9 | 777 mm |
| Lever arm 11 | 305 mm |
| Lever arm 12 | 300 mm |
| Rod 14 | 563 mm |

The distance between the bearing 5 and the articulation 15 was 813 mm. Articulation 15 was positioned 79 mm above the floor. Bearing 5 was positioned 553 mm above the floor. The distance between bearing 17 and bearing 5 was 326 mm. The angle between the connecting line 17-5 was 67°. The angle between the lever arms 11 and 12 was 172°. The plane parallel to the table frame, in which the articulation 8 is guided, was at a distance of 9.5 mm. With this layout, a low head position of 30° could be obtained with one swivel of the table frame of 640 mm.

With the same components, a low head position of 15° could be obtained by displacing the articulation 15.

What is claimed is:

1. An examination table comprising:
   a pedestal having a horizontal axis;
   a guide pivotably mounted on the pedestal to be swiveled about the horizontal axis;
   a table top supporting frame having a longitudinal direction transverse to the horizontal axis, said frame being slidably mounted on the guide for sliding in the longitudinal direction; and
   a lever arrangement for linking the swivel motion of the guide to the longitudinal motion of the table top supporting frame;
   characterized in that the lever arrangement comprises:
   a two-arm lever pivotably mounted on the guide at a bearing spaced from the horizontal swivel axis, said two-arm lever having first and second opposite ends;
   a first rod having first and second opposite ends, the first end being pivotably connected to the first end of the two-arm lever, the second end being pivotably connected to the pedestal; and
   a second rod having first and second opposite ends, the first end being pivotably connected to the table top supporting frame, the second end being pivotably connected to the second end of the two-arm lever.

2. An examination table as claimed in claim 1, characterized in that:
   the guide is arranged between the pedestal and the table top supporting frame; and
   the two-arm lever comprises a first portion arranged between the guide and the pedestal and a second portion arranged between the guide and the table top, the first and second portions being rigidly connected to each other by way of the guide.

3. A examination table as claimed in claim 2, characterized in that when the table top supporting frame is swiveled a small distance from a vertical position, the pivotable connection between the first end of the two-arm lever and the first end of the first rod moves along a path which is approximately an arc of a circle around the horizontal swivel axis.

4. An examination table as claimed in claim 3, characterized in that when the table top supporting frame is in the vertical position, the angle between the two-arm lever and the second rod is as small as possible.

* * * * *